United States Patent [19]

Hurni et al.

[11] 4,382,076

[45] May 3, 1983

[54] HEPATITIS A ANTIBODY ASSAY

[75] Inventors: William M. Hurni; William J. Miller, both of North Wales; William J. McAleer, Ambler, all of Pa.

[73] Assignee: Merck & Co., Inc., Rahway, N.J.

[21] Appl. No.: 383,668

[22] Filed: Jun. 1, 1982

Related U.S. Application Data

[63] Continuation-in-part of Ser. No. 97,299, Nov. 26, 1979, abandoned.

[51] Int. Cl.³ .................... G01N 33/48; G01N 33/54; C12Q 1/70
[52] U.S. Cl. .................................. 436/531; 436/820; 436/545; 424/1; 424/78; 435/5; 435/7
[58] Field of Search .............................. 424/8, 12, 78; 23/230 B; 435/5, 7, 235

[56] References Cited

U.S. PATENT DOCUMENTS 4,092,116  5/1978  Giaever ........................... 424/12 X
4,164,566  8/1979  Provost ........................... 424/89 X

OTHER PUBLICATIONS

Hollos, Actamicrobiol Acad. Sci. Hung., vol. 22, 1975, pp. 168-178.
Ransom, Practical Competitive Binding Assay Methods Mosby Co., St. Louis, 1976 pp, 57-59.
Friedman, Immunoserol. in the Diag. of Inf Dis. Sym. ASM, Easton PA, 1977, University Park Press, 1979, pp. 92-103.
Abbott Lab, Antibody to Hepititis A Virus $^{125}$I (Human)/Hepatitis A Virus (Primate) HAVAB TM, Radioimmunoassay for Detection of Antibody to Hepatitis A Virus, flyer, 13 pp., Rev. Nov., 1978.

Primary Examiner—Anna P. Fagelson
Attorney, Agent, or Firm—Donald J. Perrella; Hesna J. Pfeiffer

[57] ABSTRACT

A diagnostic reagent for hepatitis A antibody is prepared by adhering hepatitis A antibody to a surface by non-specific adsorption followed by specific coupling of hepatitis A antigen to the antibody. This reagent is useful in an in vitro assay for hepatitis A antibody.

5 Claims, No Drawings

HEPATITIS A ANTIBODY ASSAY

RELATED APPLICATION

The present application is a continuation-in-part of copending application Ser. No. 97,299 filed Nov. 26, 1979, now abandoned.

BACKGROUND OF THE INVENTION

The prior art, e.g., Provost et al., Proc. Soc. Exp. Biol. Med. 142, 1257-1269 (1973) describes the detection of hepatitis A antigen in serum by means of an in vivo assay involving injecting hepatitis A containing serum into marmosets and observing the marmosets for subsequent presence of hepatitis A disease. Hepatitis A antigen has never been detected in serum by an in vitro assay.

Prior art assays for hepatitis A antibody require the use of hepatitis A antigen derived from excised liver of infected marmosets. The hepatitis A antigen is then purified. This method is very costly as the marmosets are not only expensive to purchase and maintain but are becoming increasingly scarce. The method is also time-consuming as the livers cannot be harvested until several weeks after the animal is infected.

The prior art teaches antigen assays wherein the complementary antibody is bonded to a surface and used to form an immune complex with the antigen in a test sample, Friedman et al., Immunoserology in the Diagnosis of Infectious Diseases, Sym. ASM, 1977, Univ. Park Press, pp. 92-103 (1979). Conversely, an antibody assay would be performed by bonding the complementary antigen to a surface. This procedure is unavailable in the case of an assay for hepatitis A antibody, however, as hepatitis A antigen does not adhere to the surfaces, e.g., glass and plastic, to which antigens are normally bonded.

OBJECTS OF THE INVENTION

It is accordingly, an object of the present invention to provide an in vitro assay for hepatitis A antibody which does not require antigen derived from a non-human primate. Another object is to provide a faster and more economical method of preparing a diagnostic reagent for an in vitro assay for hepatitis A antibody. These and other objects of the present invention will be apparent from the following description.

SUMMARY OF THE INVENTION

A diagnostic reagent for hepatitis A antibody is prepared by adhering hepatitis A antibody to a surface which is devoid of metallic globules by non-specific adsorption followed by specific coupling of hepatitis A antigen to the antibody. This reagent is useful in an in vitro assay for hepatitis A antibody.

DETAILED DESCRIPTION

The present invention relates to an in vitro assay for hepatitis A antibody, and to a diagnostic reagent for use in an in vitro assay for hepatitis A antibody.

According to the present invention hepatitis A antibody is adsorbed as a first layer to a suitable surface, e.g., polystyrene. Conveniently, the surface is in the form of a spherical bead. The surface need not be light transmissible and is not coated with a plurality of metal globules. The hepatitis A antibody is attached to the surface by non-specific adsorption, e.g., by incubating the surface in the presence of a hepatitis A antibody-containing liquid e.g., serum, for a time sufficient to attach the hepatitis A antibody to the surface. Typical conditions are incubating for about 24 hours at about 4° C. Preferably, the liquid is diluted about 100 to about 1,000 fold with a suitable diluent such as, for example, phosphate buffered saline (PBS) or physiological saline. Such dilutions improve adsorption of the antibody to the surface.

Following adsorption of the antibody, a protein, for example, bovine serum albumin (BSA), is added to block any remaining sites for subsequent attachment of labelled antibody.

Cell culture fluid from hepatitis A virus infected cells cultured as described in U.S. Pat. No. 4,164,566 is then added and the coated surface is incubated in the presence of the cell culture fluid for a time sufficient to attach hepatitis A antigen to the hepatitis A antibody. Typical conditions are incubating for about 24 hours at about 20° C.

The resulting reagent, a surface having an outer layer of hepatitis A antigen specifically attached to an inner layer of hepatitis A antibody may be used in conventional competitive RIA assays for hepatitis A antibody.

The following examples illustrate the present invention without, however, limiting the same thereto.

EXAMPLE 1

About 500 polystyrene beads, 6.4 mm diameter, are added to about 100 ml of a 1:100 solution of hepatitis A antibody-containing serum in PBS and incubated 24 hours at 4° C. The liquid is decanted and the beads are washed three times with physiological saline to remove unadsorbed antibody. A 1% solution of BSA, 100 ml, is added to the beads and the mixture incubated for 24 hours at 4° C. The liquid is decanted and the beads washed three times with physiological saline and two times with distilled water. The beads are air dried.

Culture fluid, 100 ml, from hepatitis A virus infected cells with 0.1% $NaN_3$ is then added to the antibody-coated beads. The beads are then incubated at 20° C. for 24 hours, washed three times with physiological saline and two times with distilled water to yield a bead having an inner layer of hepatitis A antibody and an outer layer of hepatitis A antigen specifically attached to the inner layer of hepatitis A antibody. The following table compares beads of the present invention with various control beads. The beads are evaluated using commercially obtained $^{125}I$ labelled hepatitis A antibody.

| Bead | Control Cell Culture, No Antigen Uncoated Beads | Control Cell Culture No Antigen, Antibody Coated Beads | HAV Cell Culture Fluid, Uncoated Beads | HAV Cell Culture, Antibody Coated Beads |
|---|---|---|---|---|
| 1 | 336 | 705 | 604 | 8349 |
| 2 | 348 | 861 | 582 | 7831 |
| 3 | 353 | 773 | 610 | 4361 |
| 4 | 364 | 895 | 581 | 7921 |
| 5 | 382 | 891 | 632 | 7231 |

EXAMPLE 2

One bead is added to each well of a 20-well RIA assay plate and 10 µl of each sample to be tested for hepatitis A antibody is added to one well, followed by 0.2 ml of $I^{125}$ labelled hepatitis A virus antibody.

The plate is incubated for 20 hours at 20° C. At the end of this time, each well is decanted and washed two times with 5 ml of distilled water. The beads are then counted in a gamma counter for the presence of $I^{125}$ labelled. Samples, positive or negative for hepatitis A antibody are determined by comparison to controls.

What is claimed is:

1. A method of preparing a diagnostic reagent for use in an assay for hepatitis A antibody comprising contacting an opaque or transparent surface, the surface being substantially free of metallic globules and having hepatitis A antibody adhered thereto, with a cell culture fluid containing hepatitis A antigen whereby the surface has an inner layer of hepatitis A antibody and an outer layer of hepatitis A antigen.

2. A method according to claim 1 wherein the hepatitis A antibody is attached to the surface by non-specific adsorption.

3. A method according to claim 2 wherein the antibody is attached by incubating the surface in the presence of a hepatitis A antibody-containing liquid for a time sufficient to attach hepatitis A antibody to the surface.

4. A method according to claim 3 wherein the liquid is diluted to an extent effective to increase adsorption of the antibody to the surface.

5. A method according to claim 4 wherein after adsorption of the antibody the surface is treated to block any remaining non-specific sites for attachment.

* * * * *